United States Patent
Ci

(10) Patent No.: US 10,881,126 B2
(45) Date of Patent: Jan. 5, 2021

(54) NUTRITIONAL COMPOSITION FOR PROTECTING LIVER AND METHOD FOR PREPARING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 16/600,063

(22) Filed: Oct. 11, 2019

(65) Prior Publication Data

US 2020/0037651 A1 Feb. 6, 2020

Related U.S. Application Data

(62) Division of application No. 15/934,661, filed on Mar. 23, 2018, now abandoned.

(30) Foreign Application Priority Data

Nov. 30, 2017 (CN) .......................... 2017 1 1244227

(51) Int. Cl.

| | | |
|---|---|---|
| *A61K 36/00* | (2006.01) | |
| *A23L 33/105* | (2016.01) | |
| *A61K 36/899* | (2006.01) | |
| *A61K 36/815* | (2006.01) | |
| *A61K 36/752* | (2006.01) | |
| *A61K 36/725* | (2006.01) | |
| *A23P 30/20* | (2016.01) | |
| *A23L 7/10* | (2016.01) | |
| *A23L 7/143* | (2016.01) | |

(52) U.S. Cl.
CPC ............... *A23L 33/105* (2016.08); *A23L 7/10* (2016.08); *A23L 7/143* (2016.08); *A23P 30/20* (2016.08); *A61K 36/725* (2013.01); *A61K 36/752* (2013.01); *A61K 36/815* (2013.01); *A61K 36/899* (2013.01); *A23V 2002/00* (2013.01); *A23V 2200/30* (2013.01); *A23V 2250/21* (2013.01); *A23V 2300/10* (2013.01); *A23V 2300/31* (2013.01)

(58) Field of Classification Search
CPC ....................................................... A61K 36/00
USPC .......................................................... 424/725
See application file for complete search history.

(56) References Cited

FOREIGN PATENT DOCUMENTS

CN 105595166 A * 5/2016

* cited by examiner

*Primary Examiner* — Michael V Meller
(74) *Attorney, Agent, or Firm* — Cantor Colburn LLP

(57) ABSTRACT

The present application discloses a nutritional composition for protecting liver. The nutritional composition comprises the following components of raw materials in parts by weight: indica rice 60-83, polished round-grained rice 11-29, lycium barbarum 1-4, finger citron 1.5-5, citron 0.05-0.2, and Chinese date 1-3.5. The present invention, in view of the liver's characteristics of preferring free activity and disliking depression, complies with the liver's physiological function characteristics for regulation, and provides the prescription based on the method of nourishing yin blood so as to disinhibit the liver, and it is suitable to cooperate with staple foods for long-term consumption, is easily accepted by people due to the good taste, and can achieve certain efficacies of soothing the liver and nourishing the liver.

1 Claim, 1 Drawing Sheet

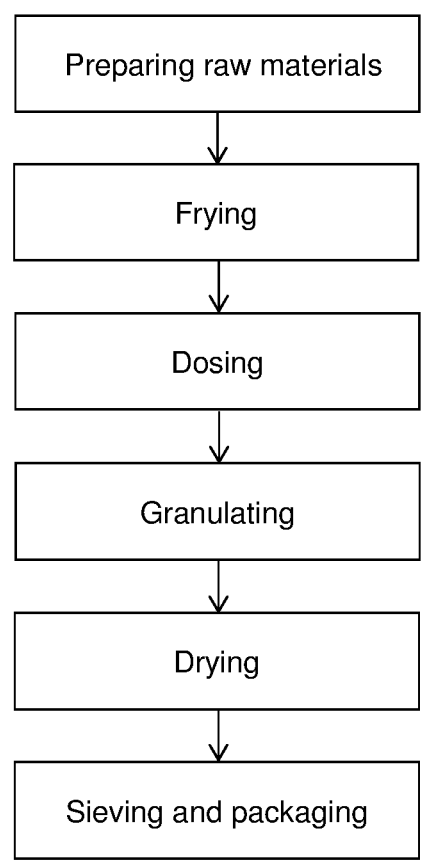

NUTRITIONAL COMPOSITION FOR PROTECTING LIVER AND METHOD FOR PREPARING THE SAME

DOMESTIC PRIORITY

This application is a divisional application of U.S. application Ser. No. 15/934,661, titled "Nutritional Composition for Protecting Liver and Method for Preparing the Same", which was filed on Mar. 23, 2018. The entire disclosures of U.S. application Ser. No. 15/934,661 are incorporated herein by reference.

TECHNICAL FIELD

The present invention belongs to the technical field of food processing, and particularly relates to a nutritional composition for protecting liver and a method for preparing the same.

BACKGROUND

Modern people are living a stressful life, with serious phenomena such as stay-up, and lack of sleep, and smoking, passive smoking, alcohol drinking, and other bad living habits cause an increased detoxification load of liver. One out of 12 Chinese has liver troubles. In recent years, more and more people suffer from liver diseases, such as fatty liver, alcoholic hepatitis, hepatitis A, hepatitis B, cirrhosis of liver, and even liver cancer, seriously affecting people's physical and psychological health.

On the basis of dietotherapy (homology between medicine and food) regimen of the traditional Chinese medical science, more and more dieticians reasonably match food materials with the homology between medicine and food, and achieve the object of protecting liver through the function of channel tropism of the food materials' four natures and five tastes.

Currently, similar health-care foods with the function of protecting liver are already available in the market, but in most cases, the matching of different foods is chaotic, does not follow the pharmacology, and has relatively bad taste.

DISCLOSURE OF THE INVENTION

A main object of the present invention is to provide a health-care food for soothing the liver and protecting the liver.

In order to achieve the above object, according to one aspect of the present invention, a nutritional composition for protecting liver is provided.

The nutritional composition for protecting liver according to the present invention includes the following components of raw materials in parts by weight: indica rice 60-83, polished round-grained rice 11-29, lycium barbarum 1-4, finger citron 1.5-5, citron 0.05-0.2, and Chinese date 1-3.5.

Furthermore, the nutritional composition for protecting liver includes the following components of raw materials in parts by weight: indica rice 65-77, polished round-grained rice 15-24, lycium barbarum 2-3, finger citron 2-3, citron 0.07-0.14, and Chinese date 2-3.

Furthermore, the nutritional composition for protecting liver includes the following components of raw materials in parts by weight: indica rice 72.4, polished round-grained rice 20, lycium barbarum 2.5, finger citron 2.5, citron 0.1, and Chinese date 2.5.

Furthermore, the nutritional composition for protecting liver further includes a Chinese herbal medicine extract of 1-3 parts, wherein the Chinese herbal medicine extract includes the following components of raw materials in parts by weight: *Citrus aurantium* L. 8-23, mint 10-26, perilla 4-18, sword bean 5-16, spina data seed 9-24, malt 12-23, dried orange peel 5-14, Chinese olive 7-18, and sterculia lychnophora 3-10.

In order to achieve the above object, according to another aspect of the present invention, a method for processing a nutritional composition for protecting liver is further provided.

The method for processing a nutritional composition for protecting liver according to the present invention includes the following steps in sequence:

step 1, preparing raw materials: purifying and sorting indica rice, polished round-grained rice, lycium barbarum, finger citron, citron, and Chinese date for subsequent use;

step 2, frying: frying respective components of raw materials under a condition of 100-200° C. for 25-120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains;

step 5, drying: drying the mixed rice grains through a microwave dryer, wherein a water content of the material is kept below 12%, and cooling the dried mixed rice grains at a room temperature;

step 6: sieving and packaging: sieving the cooled mixed rice grains, and vacuum-packaging the sieved mixed rice grains.

Furthermore, temperatures of three phases of the double-screw extruder are kept at 60° C., 90-120° C., and 90° C., respectively.

Furthermore, a heating temperature of the microwave dryer is kept at 50-60° C.

Furthermore, in a dosing process of the step 3, a Chinese herbal medicine extract of 1-3 parts is further added, and the Chinese herbal medicine extract includes the following components of raw materials in parts by weight: *Citrus aurantium* L. 8-23, mint 10-26, perilla 4-18, sword bean 5-16, spina data seed 9-24, malt 12-23, dried orange peel 5-14, Chinese olive 7-18, and sterculia lychnophora 3-10.

Furthermore, the Chinese herbal medicine extract is prepared through the following method:

drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract.

Furthermore, in a process of preparing the Chinese herbal medicine extract, a vacuum dryer is used for drying, a temperature parameter is 75° C.–80° C., and a vacuum degree is between a negative pressure of 0.08 MPa and a negative pressure of 0.1 MPa.

The present invention, in view of the liver's characteristics of preferring free activity and disliking depression, complies with the liver's physiological function characteristics for regulation, and provides the prescription based on the method of nourishing yin blood so as to disinhibit the liver, and it is suitable to cooperate with staple foods for long-term consumption, is easily accepted by people due to the good taste, and can achieve certain efficacies of soothing the liver, nourishing the liver, and protecting the liver.

BRIEF DESCRIPTION OF DRAWINGS

The FIGURE, constituting a portion of the present application, is used for further understanding of the present invention, so as to make it more obvious other features, objects, and advantages of the present application. Exemplary examples of the present invention, drawings, and description thereof are used to explain the present invention, rather than improperly limiting the present invention. In the FIGURE, FIG. 1 is a flow chart of a technology for processing a nutritional composition for protecting liver of examples of the present invention.

DETAILED DESCRIPTION OF EMBODIMENTS

In order to make a person skilled in the art better understand solutions of the present application, below technical solutions of the examples of the present application will be described clearly and completely in conjunction with the FIGURE of the examples of the present application. Apparently, some but not all of examples of the present application are described. Based on the examples of the present application, all the other examples, which a person ordinarily skilled in the art obtains without paying inventive effort, fall within the scope of protection of the present application.

Besides, the term "include (comprise)" and any variants thereof are intended to cover non-exclusive containing, for example, a product including a series of raw materials or a method including a series of steps is not necessarily limited to listing those raw materials or steps, but may include other steps or raw materials which are not clearly listed or inherent to the method or product.

It should be indicated that examples of the present application and features in the examples can be combined with each other without conflict. The present application will be described in detail with reference to the FIGURES in conjunction with the examples.

A main object of the present invention is to provide a health-care food for soothing the liver and protecting the liver.

In one aspect, the present invention provides a nutritional composition for protecting liver having this function, including the following components of raw materials in parts by weight: indica rice 60-83, polished round-grained rice 11-29, lycium barbarum 1-4, finger citron 1.5-5, citron 0.05-0.2, and Chinese date 1-3.5.

Indica rice: the traditional Chinese medical science holds that indica rice is sweet in taste and warm in nature, exerts the curative effect through the heart, spleen, and lung channels, warms the middle energizer and supplements qi (vital energy), tonifies the spleen and cures diarrhea, and is used for treatment of deficiency-cold in spleen and stomach.

Polished round-grained rice: polished round-grained rice, mild in nature and sweet in taste, exerts the curative effect through the spleen and stomach channels, and nourishes the vitality of lower energizer.

Lycium barbarum: lycium barbarum, sweet in taste and mild in nature, exerts the curative effect through the liver and kidney channels, nourishes the livers and kidneys, and replenishes the vital essence to improve eyesight, and is used for treatment of symptoms of liver-kidney yin deficiency. Lycium barbarum is sweet and natural in taste and moist, nourishes the livers and kidneys, serves the function of nourishing and building up the body, and can be applied to various symptoms of liver-kidney yin deficiency.

Finger citron: finger citron, acrid, bitter, and sour in taste and warm in nature, exerts the curative effect through the liver, spleen, stomach, and lung channels, has the efficacy of soothing the liver and regulating qi, harmonizing the stomach to relieve pain, eliminating dampness and phlegm, and is used for treatment of qi-stagnation in the liver and stomach, distending pain in chest and hypochondrium, stomach distention and fullness, reduced appetite and vomiting, and cough and excessive phlegm.

Citron: citron, acrid, bitter, and sour in taste and warm in nature, exerts the curative effect through the liver, spleen, and lung channels, soothes the liver and regulates qi, regulates the middle energizer, eliminates phlegm, and is used for treatment of qi-stagnation in the liver and stomach, distending pain in chest and hypochondrium, abdominal distention and fullness, vomiting and eructation, excessive phlegm and cough.

Chinese date: Chinese date, sweet in taste and warm in nature, exerts the curative effect through the spleen and stomach channels, nourishes the middle energizer and supplements qi, nourishes the blood for tranquilization, and is used for treatment of weakness of the spleen and the stomach, reduced appetite and loose stool, fatigue and lack of strength, deficiency of qi and blood, palpitation, allergic purpura, and hysteria of woman, and can alleviate the toxicity of strong drugs, and reduce the side effect.

The nutritional composition for protecting liver of the present invention achieves a perfect combination of dietotherapy and medical therapy by scientifically matching the principle of medicinal and edible dual purposes in combination with reasonable traditional Chinese medicines, reflecting the traditional preparing characteristics of the Chinese herbal medicine and providing the prescription based on the theory of the traditional Chinese medical science, and further enriching the purposes of the nutritional composition for protecting liver, i.e. regulation, balancing, supplementation, and keeping fit. It has the main efficacy of protecting liver. The above composition can be taken as daily regulation diet.

On the basis of the above examples, the nutritional composition for protecting liver further includes a Chinese herbal medicine extract of 1-3 parts, wherein the Chinese herbal medicine extract includes the following components of raw materials in parts by weight: *Citrus aurantium* L. 8-23, mint 10-26, perilla 4-18, sword bean 5-16, spina data seed 9-24, malt 12-23, dried orange peel 5-14, Chinese olive 7-18, and sterculia lychnophora 3-10.

Mint: mint, acrid in taste and cold in nature, exerts the curative effect through the lung and liver channels, dispels wind and heat, clears and disinhibits the head and eyes, relieves sore throat and promotes eruption, soothes the liver, promotes the circulation of qi, and is used for the treatment of common cold due to wind-heat, headache, swollen sore throat, dyspepsia and flatulence, aphtha, toothache, furuncle, urticarial, beginning of warm diseases, rubella pruritus, liver depression and qi stagnation, chest distress and hypochondriac pain.

*Citrus aurantium* L.: *Citrus aurantium* L., sweet and slightly bitter in taste and mild in nature, promotes the circulation of qi to regulate the middle energizer, promotes the digestion, eliminates the phlegm, and is used for treatment of depression and distending pain in chest and abdomen, indigestion, phlegm-fluid retention, rectocele, liver soothing, stomach harmonizing, qi regulation, stuffiness distress in the chest, abdominal distention, vomiting, and reduced appetite.

Perilla: perilla, acrid in taste and warm in nature, exerts the curative effect through the lung and spleen channels, relieves exterior syndrome by diaphoresis, promotes the circulation of qi and harmonizes stomach, and is used for treatment of common cold due to wind-cold, cough and nausea in the abdomen, pregnancy vomiting, and fish and crab poisoning.

Sword bean: sword bean, sweet in taste and warm in nature, exerts the curative effect through the stomach and kidney channels, warms the middle energizer, descends qi, relieves hiccup, and is used for treatment of deficiency-cold hiccup and vomiting.

Spina data seed: spina data seed, sweet and sour in taste and mild in nature, exerts the curative effect through the heart, spleen, liver, and gallbladder channels, nourishes the liver, calms the heart, soothes the nerves, arrests sweating, and is used for the treatment of dysphoria insomnia, palpitation, body deficiency and spontaneous perspiration, and night sweating.

Malt: malt, sweet in taste and mild in nature, exerts the curative effect through the spleen and stomach channels, promotes the circulation of qi and digestion, tonifies the spleens, stimulates appetite, terminates lactation, and relieves flatulence, and is used for treatment of indigestion, abdominal distention, reduced spleen-deficiency appetite, milk stasis, breast tenderness, delectation of women, liver depression and hypochondriac pain, and stomachache due to emotional depression and the hyperactive liver-qi attacking the stomach.

Dried orange peel: dried orange peel, acrid and slightly bitter in taste and warm in nature, exerts the curative effect through the spleen and lung channels, has the efficacy of regulating qi and middle energizer, removing dampness to reduce phlegm, and can be used for treatment of qi stagnation of spleen and stomach, abdominal fullness and distention, vomiting, or chest distress, anorexia, and loose stool caused by retention of damp-turbid substance, but should be used with caution for people with yin and body fluid deficiency and excessive heat inside.

Chinese olive: Chinese olive, sweet and sour in taste and mild in nature, exerts the curative effect through the lung and stomach channels, clears away heat and toxic materials, relieves sore throat, generates the body fluid, and is used for treatment of swollen sore throat, cough and sticky phlegm, vexation heat and thirst, and fish and crab poisoning.

Sterculia lychnophora: sterculia lychnophora, sweet in taste and cold in nature, exerts the curative effect through the lung and large intestine channels, clears away heat and moistens the lung, relieves sore throat and eases up the voice, relaxes bowel, and is used for treatment of lung heat and celostomia, dry cough without phlegm, sore dry throat, heat accumulation constipation, headache and hot eyes.

A small amount of the Chinese herbal medicine extract is added to the nutritional composition for protecting liver for further enhancing the function of the nutritional composition for soothing the liver and regulating qi. In the prescription, mint and *Citrus aurantium* L soothe the liver and promote circulation of qi; spina data seed nourishes the liver and soothes the nerves; the dried orange peel regulates qi and middle energizer, malt promotes the circulation of qi and digestion, and the dried orange peel and malt together have the effect of promoting qi movement; sword bean warms the middle energizer and descends qi; Chinese olive and sterculia lychnophora clear away heat and toxic materials and generate the body fluid, and can alleviate the strong property of the Chinese herbal medicine extract, being nutritious but not greasy. By using these drugs in combination, the effect of soothing the liver and regulating qi can be achieved. Moreover, the usage amount of the Chinese herbal medicine extract is relatively small, then it will not destroy the nutritional structure of the original nutritional composition for protecting liver, and will not produce an undesirable taste.

As shown in FIG. 1, a method for preparing the nutritional composition for protecting liver includes the following steps in sequence:

step 1, preparing raw materials: purifying and sorting indica rice, polished round-grained rice, lycium barbarum, finger citron, citron, and Chinese date for subsequent use, wherein the raw materials are strictly checked, and impurities and soils are removed, effectively reducing remnant of pollutants such as heavy metals and pesticides;

step 2, frying: frying respective components of raw materials under a condition of 100-200° C. for 25-120 min, wherein the temperature should not be too high to make starchy foods produce acrylamide, thus preventing loss of nutrients;

step 3, dosing: grinding the respective fried raw materials, then mixing and stirring evenly the respective ground raw materials according to proportions to obtain a rice powder, wherein the proportions of the respective raw materials are based on the prescription of the nutritional composition for protecting liver of the present invention, and in the dosing process, a Chinese herbal medicine extract of 1-3 parts can be further added, and the Chinese herbal medicine extract includes the following components of raw materials in parts by weight: *Citrus aurantium* L. 8-23, mint 10-26, perilla 4-18, sword bean 5-16, spina data seed 9-24, malt 12-23, dried orange peel 5-14, Chinese olive 7-18, and sterculia lychnophora 3-10. Specifically, the Chinese herbal medicine extract can be prepared through the following method: drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract. In the process of preparing the Chinese herbal medicine extract, a vacuum dryer is used for drying, a temperature parameter is 75° C.–80° C., and a vacuum degree is between a negative pressure of 0.08 MPa and a negative pressure of 0.1 MPa;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90-120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50-60° C.;

step 6: sieving and packaging: sieving the cooled mixed rice grains, and vacuum-packaging the sieved mixed rice grains, wherein the appearance and homogeneity of product particles can be improved by sieving, and in practical operation, after the packaging is completed, a product name, a product lot number, specification, net weight, date of manufacture, name of position, and person in charge are recorded and tagged, and a delivery receipt is filled in, then the product is transferred to an intermediate station.

Example 1

A nutritional composition for protecting liver includes the following components of raw materials in parts by weight: indica rice 60, polished round-grained rice 11, lycium barbarum 1, finger citron 1.5, citron 0.05, and Chinese date 1.

A preparation method is as follows:

step 1, preparing raw materials: purifying and sorting indica rice, polished round-grained rice, lycium barbarum, finger citron, citron, and Chinese date for subsequent use;

step 2, frying: frying respective components of raw materials under a condition of 100° C. for 120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50° C.;

step 6: sieving and packaging: sieving the cooled mixed rice grains, and vacuum-packaging the sieved mixed rice grains.

Example 2

A nutritional composition for protecting liver includes the following components of raw materials in parts by weight: indica rice 83, polished round-grained rice 29, lycium barbarum 4, finger citron 5, citron 0.2, and Chinese date 3.5.

A preparation method is as follows:

step 1, preparing raw materials: purifying and sorting indica rice, polished round-grained rice, lycium barbarum, finger citron, citron, and Chinese date for subsequent use;

step 2, frying: frying respective components of raw materials under a condition of 200° C. for 25 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 60° C.;

step 6: sieving and packaging: sieving the cooled mixed rice grains, and vacuum-packaging the sieved mixed rice grains.

Example 3

A nutritional composition for protecting liver includes the following components of raw materials in parts by weight: indica rice 65, polished round-grained rice 15, lycium barbarum 2, finger citron 2, citron 0.07, and Chinese date 2.

A preparation method is as follows:

step 1, preparing raw materials: purifying and sorting indica rice, polished round-grained rice, lycium barbarum, finger citron, citron, and Chinese date for subsequent use;

step 2, frying: frying respective components of raw materials under a condition of 120° C. for 80 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 100° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 58° C.;

step 6: sieving and packaging: sieving the cooled mixed rice grains, and vacuum-packaging the sieved mixed rice grains.

Example 4

A nutritional composition for protecting liver includes the following components of raw materials in parts by weight: indica rice 77, polished round-grained rice 24, lycium barbarum 3, finger citron 3, citron 0.14, and Chinese date 3.

A preparation method is as follows:

step 1, preparing raw materials: purifying and sorting indica rice, polished round-grained rice, lycium barbarum, finger citron, citron, and Chinese date for subsequent use;

step 2, frying: frying respective components of raw materials under a condition of 130° C. for 60 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 105° C., and 90° C., respectively;

step 5: drying: drying the mixed rice grains through a microwave dryer, wherein a water content of the material is kept below 12%, cooling the dried mixed rice grains at a room temperature, wherein a heating temperature of the microwave dryer is kept at 53° C.;

step 6: sieving and packaging: sieving the cooled mixed rice grains, and vacuum-packaging the sieved mixed rice grains.

Example 5

A nutritional composition for protecting liver includes the following components of raw materials in parts by weight: indica rice 72.4, polished round-grained rice 20, lycium barbarum 2.5, finger citron 2.5, citron 0.1, and Chinese date 2.5.

A preparation method is as follows:

step 1, preparing raw materials: purifying and sorting indica rice, polished round-grained rice, lycium barbarum, finger citron, citron, and Chinese date for subsequent use;

step 2, frying: frying respective components of raw materials under a condition of 150° C. for 40 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 6

A nutritional composition for protecting liver includes the following components of raw materials in parts by weight: indica rice 72.4, polished round-grained rice 20, lycium barbarum 2.5, finger citron 2.5, citron 0.1, Chinese date 2.5, and a Chinese herbal medicine extract 1. The Chinese herbal medicine extract includes the following components of raw materials in parts by weight: Citrus aurantium L. 8, mint 10, perilla 4, sword bean 5, spina data seed 9, malt 12, dried orange peel 5, Chinese olive 7, and sterculia lychnophora 3. The Chinese herbal medicine extract is prepared through the following method: drying and grinding respective raw materials into a medicinal powder, subjecting the medicinal powder to ultrasonic extraction, centrifugation, and concentration with an ethanol solution of 65% in volume percentage to obtain the Chinese herbal medicine extract. In the process of preparing the Chinese herbal medicine extract, a vacuum dryer is used for drying, a temperature parameter is 75° C., and a vacuum degree is a negative pressure of 0.08 MPa.

A method for preparing the nutritional composition for protecting liver is as follows:

step 1, preparing raw materials: purifying and sorting indica rice, polished round-grained rice, lycium barbarum, finger citron, citron, and Chinese date for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 7

A nutritional composition for protecting liver includes the following components of raw materials in parts by weight: indica rice 72.4, polished round-grained rice 20, lycium barbarum 2.5, finger citron 2.5, citron 0.1, Chinese date 2.5, and a Chinese herbal medicine extract 1. The Chinese herbal medicine extract includes the following components of raw materials in parts by weight: Citrus aurantium L. 23, mint 26, perilla 18, sword bean 16, spina data seed 24, malt 23, dried orange peel 14, Chinese olive 18, and sterculia lychnophora 10. The Chinese herbal medicine extract is prepared through the following method: drying and grinding respective raw materials into a medicinal powder, subjecting the medicinal powder to ultrasonic extraction, centrifugation, and concentration with an ethanol solution of 40% in volume percentage to obtain the Chinese herbal medicine extract. In the process of preparing the Chinese herbal medicine extract, a vacuum dryer is used for drying, a temperature parameter is 80° C., and a vacuum degree is a negative pressure of 0.1 MPa.

A method for preparing the nutritional composition for protecting liver is as follows:

step 1, preparing raw materials: purifying and sorting indica rice, polished round-grained rice, lycium barbarum, finger citron, citron, and Chinese date for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Experiment Example 1: Sensory Evaluation of Eating Quality

Evaluating method: scoring is made in comparison with reference samples according to the odor, appearance structure, palatability, taste, and cold rice texture of the rice, and an overall score is a sum of respective items. Scoring rules are shown in Table 1. Products used for the sensory evaluation of this experiment example are staple foods, numbered as products 1 to 7, obtained by mixing the nutritional compositions for tonifying kidney obtained in Examples 1 to 7 of the present invention with indica rice, respectively, a mixing ratio of the indica rice to the nutritional composition for protecting liver being 4:1. Statistical results of the evaluation scores corresponding to the products 1 to 7 are shown in Table 2.

Regarding the overall score, less than 50 indicates "very bad", 51-60 "bad", 61-70 "ordinary", 71-80 "relatively good", 81-90 "good", and more than 90 "excellent".

Uncovered matters such as specific operation steps, preparation work, evaluator determination, sample approval, instrument, and appliance should comply with GB/T 15682-

2008 Inspection of Grain and Oils—Method for Sensory Evaluation of Paddy or Indica Rice Cooking and Eating Quality.

TABLE 1

Scoring Rules for Sensory Evaluation of Steamed Rice

| First-grade Index Score | Second-grade Index Score | Description of specific properties: score |
|---|---|---|
| Odor 20 | Authenticity and Intensity 20 | Having unique aroma of steamed rice, rich in fragrance: 18~20 |
| | | Having unique aroma of steamed rice, delicate in fragrance of steamed rice: 15~17 |
| | | Having unique aroma of steamed rice, but not obvious in fragrance: 12~14 |
| | | Having no fragrance, but without undesirable odor: 7~12 |
| | | having an undesirable odor: 0~6 |
| Appearance Structure 20 | Color 7 | Bright in color: 6~7 |
| | | Normal in color: 4~5 |
| | | Dull in color: 0~3 |
| | Gloss 8 | Having obvious gloss: 7~8 |
| | | Slightly glossy: 5~6 |
| | | Having no gloss: 0~4 |
| | Integrity of Steamed Rice Grain 5 | Compact steamed rice structure, good integrity of steamed rice grain: 4~5 |
| | | Most of the steamed rice having a compact and complete structure: 3 |
| | | Some steamed rice grains explode: 0~2 |
| Palatability 30 | Viscosity 10 | Smooth, Viscous, not sticky to teeth: 8~10 |
| | | Viscous, basically not sticky to teeth: 6~7 |
| | | Viscous, sticky to teeth; or not viscous: 0~5 |
| | Elasticity 10 | Chewy: 8~10 |
| | | Slightly shewy: 6~7 |
| | | Loose, hard, feeling foreign matters present: 0~5 |
| | Hardness 10 | Neither too hard nor too soft: 8~10 |
| | | Slightly hard or slightly soft: 6~7 |
| | | Very hard or very soft: 0~5 |
| Taste 25 | Authenticity and Persistence 25 | Having relatively strong fragrance and sweet taste when chewed: 22~25 |
| | | Having light fragrance and sweet taste when chewed: 18~21 |
| | | Having no fragrance or sweet taste when chewed, but without undesirable odor: 16~17 |
| | | Having no fragrance or sweet taste when chewed, but having an undesirable odor: 0~15 |
| Cold Steamed Rice Texture 5 | Agglomeration, Viscoelasticity, and Hardness 5 | Relatively loose, relatively good in viscoelasticity, moderate in hardness: 4~5 |
| | | Agglomerated, slightly bad in viscoelasticity, slightly hardened: 2~3 |
| | | Hardened, bad in viscoelasticity, and more rigid: 0~1 |

TABLE 2

Statistical Table of Results of Evaluation Scores of Respective Products

| Group | Overall Score/Score | Evaluation Result |
|---|---|---|
| Product 1 | 88 | Good |
| Product 2 | 93 | Excellent |
| Product 3 | 95 | Excellent |
| Product 4 | 92 | Excellent |
| Product 5 | 89 | Good |
| Product 6 | 90 | Excellent |
| Product 7 | 91 | Excellent |

It can be seen from the above test results that all the sensory evaluation results made by respective sensory evaluators on the nutritional compositions for tonifying kidney prepared in Examples 1 to 7 in conjunction with indica rice are "excellent" and "good". It is indicated that the products of the present invention have relatively excellent performances in odor, appearance structure, palatability, taste, and cold rice texture.

Experiment Example 2: Protecting Effect of the Nutritional Composition for Protecting Liver on Chemical Liver Injury Experiment method: kunming mice, half males and half females, with a body weight of 20±2 g, were randomly divided into one control (normally fed) group, one model group (set up as liver-injury models with carbon tetrachloride), and five experiment groups (groups of the nutritional compositions obtained in Examples 1-7), 10 mice in each group; normal saline (10 mL/kg of the body weight of the mouse) was given to the mice in the control group and the model group, and the five experiment groups were administrated with corresponding dietotherapy electuaries by gavage once a day by 2 g/100 g of body weight, for 7 days in total. After the last time of administration by gavage, the mice fasted but could drink water for 4 h, and except the control group, the mice in the other groups were orally administrated with 0.1% $CCl_4$ 0.2 mL/10 g, followed by fasting for 24 h, and then decapitated. The blood was taken for serum segregation to detect the activity of serum alanine aminotransferase (ALT) according to Reitman-Frankel; the liver was taken and rinsed with cold normal saline to be prepared into a liver homogenate of 10%, and the content of malondialdehyde (MDA) was measured according to the thiobarbituric acid (TBA) colorimetry, and the activity of superoxide dismutase (SOD) was measured according to the xanthinoxidase method. Results are shown in the following Table 3.

TABLE 3

Influence of Nutritional Compositions on Serum ALT Activity, Liver MDA Content, and SOD Activity of Liver-injured Mice

| Group | ALT (U/L) | SOD (NU/mL) | MDA (nmol/mL) |
|---|---|---|---|
| Control Group | 42.9 ± 3.9 | 22.9 ± 4.38 | 170.8 ± 5.38 |
| Model Group | 153.3 ± 19.3▲ | 42.9 ± 5.67▲ | 91.7 ± 4.69▲ |

TABLE 3-continued

Influence of Nutritional Compositions on Serum ALT Activity,
Liver MDA Content, and SOD Activity of Liver-injured Mice

| Group | ALT (U/L) | SOD (NU/mL) | MDA (nmol/mL) |
|---|---|---|---|
| Example 1 | 126.5 ± 22.6** | 35.6 ± 4.47** | 149.7 ± 5.22* |
| Example 2 | 118.7 ± 23.1** | 33.8 ± 3.33** | 138.5 ± 5.17** |
| Example 3 | 146.3 ± 28.1* | 28.7 ± 4.27** | 151.2 ± 6.08** |
| Example 4 | 109.8 ± 26.2** | 36.2 ± 5.96* | 149.3 ± 4.59** |
| Example 5 | 118.4 ± 21.9** | 27.6 ± 5.08** | 155.8 ± 4.54** |
| Example 6 | 104.9 ± 24.8** | 24.8 ± 3.29** | 161.3 ± 5.26** |
| Example 7 | 99.8 ± 18.7** | 25.2 ± 4.17** | 159.9 ± 5.84** |

Notes:
compared with the model group,
*P < 0.05,
**P < 0.01; compared with the control group,
▲P < 0.05.

It can be seen from Table 3 that compared with the control group, the serum ALT activity of the mice in the model group is significantly improved, and the administration of the nutritional compositions of Examples 1 to 7 can significantly inhibit the level of serum ALT from increasing. The experiment also shows that after injury with $CCl_4$, the MDA content of the liver homogenate of the mice is evidently increased, and the SOD activity is decreased prominently, while for the mice administrated with the nutritional compositions of Examples 1 to 7, the MDA content of the liver homogenate is evidently decreased, and the SOD activity is increased prominently. It is indicated that the nutritional compositions of Examples 1 to 7 can enhance the anti-injury capability of the hepatic cells, and have certain protecting effect to the liver.

The foregoing only describes preferred examples of the present invention and is not intended to limit the present invention. For a person skilled in the art, various modifications and variations may be made to the present invention. Any modifications, equivalent replacements, improvements, etc., made within the spirit and principle of the present invention, should be covered by the scope of protection of the present invention.

What is claimed is:

1. A method for preparing a vacuum packed dried gelantinized powder consisting essentially of:
   a) purifying and sorting indica rice, polished round-grained rice, lycium barbarum, finger citron, citron, and a chin se date to create a mixture;
   b) frying the mixture at 100° C.-200° C. for 25-120 min to create a fried mixture;
   c) grinding the fried mixture with Citrus aurantium, mint, perilla, sword bean, spina date seed, malt, dried orange peel, Chinese olive, and sterculia lychnophora, then mixing and stirring evenly to yield a grinded fried mixture;
   d) granulating and extruding the grinded fried mixture through a double-screw extruder, followed by gelatinization and granulation, to obtain a gelantinized powder;
   d) drying the gelantinized powder with a microwave dryer, wherein the water content of the dried gelantinized powder is kept below 12%, then cooling the dried gelantinized powder at room temperature; and
   e) sieving and packaging the dried gelantinized powder and vacuum packaging the dried gelantinized powder.

* * * * *